United States Patent [19]
Forberg

[11] 3,993,068
[45] Nov. 23, 1976

[54] PIERCING CANNULA OF INFUSION AND TRANSFUSION INSTRUMENTS

[75] Inventor: Hans-Jürgen Forberg, Lensahn, Holst., Germany

[73] Assignee: Transcodan Sven Husted-Andersen, Germany

[22] Filed: July 8, 1975

[21] Appl. No.: 594,064

[30] Foreign Application Priority Data
July 13, 1974 Germany............................ 2433780
June 27, 1975 Germany............................ 2528738

[52] U.S. Cl............................................ 128/214 C
[51] Int. Cl.².......................................... A61M 5/16
[58] Field of Search......... 128/214 R, 214 C, 214.2, 128/221, 252, 275

[56] References Cited
UNITED STATES PATENTS

| | | | |
|---|---|---|---|
| 2,884,924 | 5/1959 | Shaw | 128/214 C |
| 3,493,139 | 2/1970 | Faddoul et al. | 128/252 X |
| 3,662,752 | 5/1972 | Yokoyama | 128/214 R |
| 3,822,700 | 7/1974 | Pennington | 128/214 C |

*Primary Examiner*—Dalton L. Truluck
*Attorney, Agent, or Firm*—McGlew and Tuttle

[57] ABSTRACT

A piercing cannula of infusion and transfusion instruments, includes a housing having a lower liquid chamber defined therein and having an upper closure with an air opening on one side. A liquid member communicating with the interior of the housing extends outwardly through the closure directly alongside an aeration channel which has a lower end communicating with the opening. The housing includes a tubular portion defining an air inlet passage from the opening to the lower end of the aeration channel and a valve member is disposed between the liquid chamber and the lower end of the open aeration channel. The valve member comprises an upper inwardly tapered portion which is resiliently biased against the end of the tubular part defining the air passage.

11 Claims, 3 Drawing Figures

PIERCING CANNULA OF INFUSION AND TRANSFUSION INSTRUMENTS

FIELD AND BACKGROUND OF THE INVENTION

This invention relates in general to the construction of cannulae and, in particular, to a new and useful piercing cannula of infusion and transfusion instruments which includes a liquid channel and an aeration channel which terminates in an aperture leading into the open and an aperture at its lower end which is closed by a valve of elastic material leading through a lateral air passage.

DESCRIPTION OF THE PRIOR ART

Closures for bottles for the storage, preparation, sterilization and dispensing of medicinal liquids, which are provided with a dispensing channel and an aeration channel are known. Through the dispensing channel may be inserted, for example, the piercing cannula of a drip chamber. The aeration channel is closed at its aperture opening into the interior of the bottle by a check valve formed by an elastic blade. A similar closure is known wherein an air filter is arranged in the aeration channel and an annular membrane forming a check valve of thin elastic material is employed to lift off its seat toward the interior of the container and in so doing clear the passage openings when a negative pressure is produced. A device of this type is shown in U.S. Pat. No. 2,770,234. A further known device is a closure for bottles which is provided with an aeration device which contains an air filter and a check valve. The check valve is formed by a hose piece which comprises a rubber which terminates at its end in two contiguous blades. The blades permit discharge of air only in one direction and act as a check valve.

Also known is a drip chamber for infusion and transfusion instruments which is provided with a piercing cannula which contains both a liquid channel and an aeration channel. In the aeration channel, a filter and a valve operating without separate mechanical parts is known. In this construction, the valve is formed in the manner of a Bunsen valve from a rubber-elastic material. A Bunsen valve consists of a glass tube section which carries at one end a piece of thick, hermetically closing rubber hose. The hose is closed off at its other end by a fitting glass piece inserted in a gas-tight manner. In the intermediate zone, the rubber hose is provided with a sharp longitudinal cut.

Finally, an infusion device is known which consists of a needle body which is traversed by a central bore for the flow of fluid medicament. The needle body presents an inlet groove for air and is surrounded by a sheath which carries a branch cylinder or a nipple in which can be inserted a cylindrical insert containing a check valve. Air or a necessary liquid additive medicament can enter only in the inlet direction via the cylindrical insert, the check valve and the inlet groove. The check valve comprises a spherical or similarly shaped hollow head portion of a flexible material, such as rubber or plastic. The plastic material has a slot on its front end and a nipple on its back and is made of a piece of the same material as the spherical head portion. Air or liquid can pass through this check valve only in the nipple direction and spherical head portion slot.

SUMMARY OF THE INVENTION

The present invention provides a check valve of simple design which is easy and inexpensive to manufacture and to insert in the instrument and which operates satisfactorily and closes the non-return rabbet tightly and also presents only a slight resistance to the air in case of opening. Moreover, in the interest of a rapid air supply, the check valve is able to close a large aeration aperture. In addition, upon backflow of the liquid into the aeration channel, the valve is of an arrangement and construction such that it will not be subject to operating troubles.

The invention comprises a valve which has an upper portion or component of wedge-shape cross-section which applies against the aperture for the aeration air under the force of its own resilience. The valve has the advantage of a simple construction and a simple mode of manufacture and may be easily installed. The valve is formed by the movable component which comprises a rubber-elastic material and by a peripheral portion of the aperture which leads out so that, when closing, the rubber-elastic valve component applies against a rigid component. A satisfactory closure is thereby ensured. The valve offers little resistance, in particular also the aperture leading into the open can be given a large cross-section since the movable valve component can be designed of corresponding dimensions without difficulty. Thus, a relatively large area of attack is formed, so that the valve opens satisfactorily even at low pressures and constitutes a slight resistance to the inflowing air. Consequently, air can flow in rapidly and the liquid can flow off rapidly. The valve is suitable both for normal infusion and transfusion, as well as for carrying out pressure infusion and pressure transfusion.

An advantageous embodiment of the construction employs a valve body having a tapered part which is directed upwardly. The aeration channel which is defined in the closure portion of the piercing cannula container advantageously ends below the aperture closed by the elastic valve component. In this way, it is avoided that solution entering the liquid channel gets to the valve area so that there is no danger that it will cause a sticking of the parts or increase the resistance of the operation of the valve. An elastic valve component a wedge-shape cross-section may have various forms. A very simple structural form comprises an elastic valve component of cylindrical shape with a cross-section being cuneiform in a plane passing through the axis of the cylinder. Such a valve component may consist of a lower cylindrical part and an upper substantially cylindrical part.

According to another embodiment of the invention, the valve component may be provided in its lower part with a closure ring for the separation of liquid chamber relative to the air chamber. In this form, the liquid channel traverses the valve component which constitutes, at the same time, the seal of the liquid channel and, hence, the seal between the two chambers.

In addition, the cylindrical valve component may be provided with an annularly projecting enlargement in its lower zone on its outside. In this manner, the valve component does not apply on its entire substantially cylindrical outer face against the inner wall of the piercing cannula in the zone of the aperature which leads out to the atmosphere, so that the surface of the valve component activated by external pressure is enlarged. For the same purpose, the inner wall of the piercing cannula may be provided with an annular recess in the zone of the aperture leading into the open and the elastic valve component may apply only by its upper end against the projection formed above the annular recess.

In a further embodiment of the invention, the closure member which seals the container housing is constructed with an elongated skirt having an opening below the air opening, for example, which is provided for the introduction of another fluid into the system through such opening. In this embodiment, the valve member is elongated so that it closes off both the fluid opening and the air opening. The construction is such that a solution in addition to the air may be introduced through the aperture into the infusion or transfusion instrument and will flow through the aeration channel into the bottle for storage, preparation or the like of medicinal liquids. Consequently, additional medicinal liquids can be mixed during an infusion or transfusion. The fluid opening may be closed by a cap or other suitable device.

Accordingly, it is an object of the invention to provide a piercing cannula of infusion and transfusion instruments which comprises a housing having a lower liquid chamber for liquid and having an upper closure with an air opening and which includes a tubular liquid member communicating with the interior of the housing and extending outwardly through the closure and an aeration channel adjacent the liquid channel which also extends through the closure and has a lower end opening into the closure adjacent an inner end of a tubular part which defines an air passage from the air opening to the lower end opening of the closure and which also includes a valve member disposed between the liquid chamber and the lower open end of the aeration channel and includes a resilient wedge-shape portion biased against the tubular part to close the air passage.

A further object of the invention is to provide a piercing cannula which is simple in design, rugged in construction and economical to manufacture.

For an understanding of the principles of the invention, reference is made to the following description of typical embodiments thereof as illustrated in the accompanying drawing.

DESCRIPTION OF THE PREFERRED EMBODIMENTS

Figure 1:
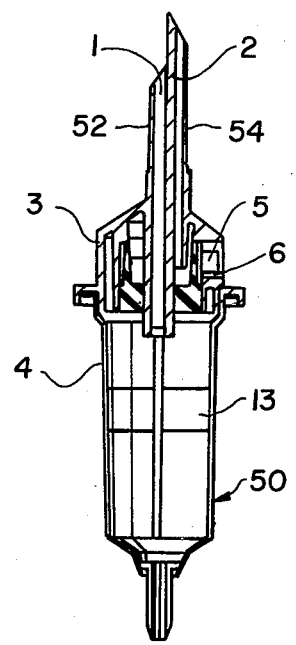
FIG. 1 is a transverse sectional view of a piercing cannula having a contiguous drip chamber constructed in accordance with the invention.
Figure 2:
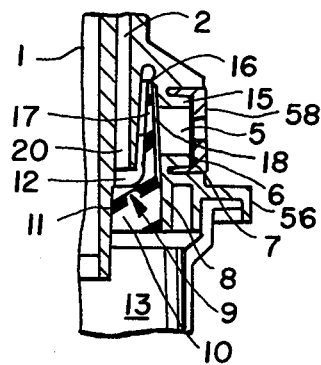
FIG. 2 is an enlarged transverse section of a portion of the cannula shown in FIG. 1.

Referring to the drawings in particular, the invention embodied therein, comprises a cannula, generally designated 50, which includes a housing 4, defining a liquid chamber 13 which is closed on the top by a connection piece or closure 3 which carries a first or liquid tubular member 52 having a passage 1 for liquid and a second tubular member 54 directly alongside the first tubular member which defines an aeration passage 2. The closure includes a flange portion 56 which engages over a housing portion 4, and it carries an inner annular wall 8 which is below a lower end 20 of the aeration channel 2. The closure part or connection piece 3 includes a lateral opening 5 defined in a ring member 58 which is threaded onto a tubular housing portion 15 which defines an air flow passage from the opening 5 inwardly to an air chamber 12 which is blocked by an elastic valve member or valve component 9.

In the embodiment shown, the valve component 9 comprises an annular member having an inner cylindrical wall 11 which bears around the outer wall of the first tubular member 52 and is spaced downwardly below the lower end of the channel 2. The valve component also includes an upper wedge-shape portion 17 which lies directly subjacent a projection 16 defined in the interior of the housing and acts to close off the inner end of the tubular member 15. The wedge-shape portion 17 includes an upper tapered end which tapers inwardly from the inner side and it is made of resilient material so that it is biased by its own resiliency to close the opening 5 into the air chamber 12. The outer surface 18 of the valve component 9 is spaced slightly from the edge of tubular member 15. A satisfactory tight closure is provided between the upper tapered portion 17 of valve member 9 and the inner end of the air passage defined by tubular part 15. A slight spacing between the surface 18 and the end of the wall portion defines an air gap which enlarges the area of the valve components action under external pressure. As a result, the valve opens at a slight positive pressure acting from the outside. The upper portion 17 may also be made cylindrical, if desired.

The lower end 20 of aeration channel 2 lies below the inlet opening 5. This has the advantage that liquid drops which might get into the interior through the aeration channel stay in the lower zone of space 12 and do not get onto the valve surface 18 so that valve surface 18 cannot become adhered with the adjacent housing part or otherwise impair the valve action.

Valve component 9 advantageously comprises a soft and elastic material. Alternately, it may have other than the cylindrical form indicated, and may consist, for example, of a planar piece arranged in the zone of the aperture 5 similar to the disclosed embodiment. The valve seals satisfactorily at internal positive pressure as well as in a pressureless state. The manufacture of the valve component and its installation are very simple. The valve component may be slipped on from below over the lower part of the liquid channel.

Figure 3:
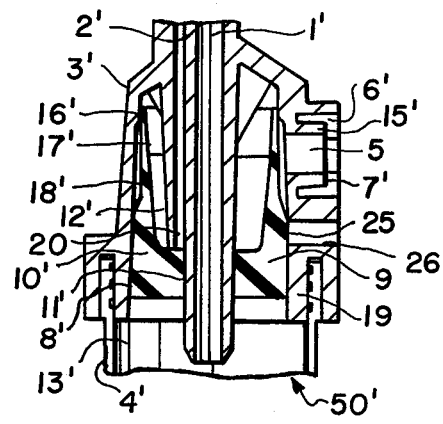
FIG. 3 is a section similar to FIG. 2 of another embodiment of the invention.

As shown in FIG. 3, a piercing cannula of infusion and transfusion instruments, generally designated 50', includes a housing 4' defining a liquid container 13' which is closed by a closure member or connecting piece housing 3' having tubular portions which define a liquid channel or conduit 1' and an aeration channel or conduit 2'. Closure member 3' includes an interior abutment 16' which engages against the upper end of a resilient tapered portion 17' of a valve component 10'. The tapered portion is held by the abutment 16' away from a surface 18' at the interior of the closure member 3'. Valve member 10' includes a base portion 9 which is located between an exterior wall 11' of the fluid conduit portion 1' and an interior wall 8' of closure member 3'. In this construction, a filter 7' is held between a threaded tubular cap 6' which is threadedly engaged over a tubular member 15' at the location of an air inlet opening 5. The interior passage defined by the tubular wall portion 15' is closed by the resilient portion 17' or the valve member 10'.

In the embodiment of FIG. 3, there is a fluid aperture 25 in one portion of the skirt of the connection piece 3', preferably lower than the air opening 5. This fluid opening 25 may be covered on the exterior by a protective cap (not shown). It may also be provided with a connection 26 projecting outwardly. Through this aperture, a piercing cannula can be passed which penetrates the valve member 10' slightly above the base portion 9' in the zone of an air chamber 12'. A medicinal liquid can be pressed into the infusion or transfusion instrument by insertion through the opening 25 and through the material of the valve member 10'. Upon finising the addition, the piercing cannula is withdrawn again and the perforation which is made in the wall of the upper portion 17' will close automatically so that air will not subsequently penetrate. The valve component 10' may be made of a soft elastic material. Its shape may be different from that which is shown, for example, it may comprise a surface element located in the zone of apertures 5 and 25 as indicated so that it will seal perfectly under internal overpressure and in a pressureless state.

While specific embodiments of the invention have been shown and described in detail to illustrate the application of the principles of the invention, it will be understood that the invention may be embodied otherwise without departing from such principles.

What is claimed is:

1. A drop chamber having a piercing cannula of infusion and transfusion instruments thereon, comprising a housing having an interior liquid chamber for liquid and a closure covering said chamber with an air opening, a tubular member for liquid passage therethrough communicating with the interior of said housing and extending outwardly through said closure, means defining an aeration channel adjacent said tubular member through said closure and having a lower end with an opening in said chamber, a tubular part defining an air passage from said opening to said chamber, a valve member disposed in said chamber between said air passage and said lower end opening of said aeration channel and including a resilient portion biased against said tubular part over the air passage and regulating the air flow therethrough, said resilient portion being of a wedge-shape configuration and said valve member includes a base portion below said resilient portion.

2. A drop chamber having piercing cannula according to claim 1, wherein the lower end portion of said aeration channel terminates below the bottom of said tubular part defining said air passage.

3. A drop chamber having piercing cannula according to claim 1, wherein said resilient portion is cylindrical.

4. A drop chamber having a piercing cannular of infusion and transfusion instruments thereon, comprising a housing having an interior liquid chamber for liquid and a closure covering said chamber with an air opening, a tubular member for liquid passage therethrough communicating with the interior of said housing and extending outwardly through said closure, means defining an aeration channel adjacent said tubular member through said closure and having a lower end with an opening in said chamber, a tubular part defining an air passage from said opening to said chamber, and a valve member disposed in said chamber between said air passage and said lower end opening of said aeration channel and including a resilient portion biased against said tubular part over the air passage and regulating the air flow therethrough, said valve member comprising an annular base portion below said tubular part closing off the space between said tubular part and the lower end of said aeration channel and the liquid chamber of said housing and said resilient portion extends upwardly from said base portion.

5. A drop chamber having a piercing cannular of infusion and transfusion instruments thereon comprising a substantially cylindrical housing having an upper opening with a flange rim and an interior defining a liquid chamber, a closure member closing the upper opening of said housing having a flange portion engaged with the rim of said housing, a tubular member for liquid passage therethrough extending through said closure member and terminating in a lower end in the liquid chamber and an exterior outer end external of said closure, a tubular aeration member adjacent said liquid member having a lower end terminating within said closure, a lateral opening in said closure member, the space below said aeration channel adjacent the lateral opening and within said closure member defining an air chamber, means defining an air passage from said opening into said air chamber, said closure member having an annular interior wall portion around the lower end of said air chamber, and a valve member comprising an annular base part engaged over said liquid tubular member and having an outer periphery engaged with said annular interior wall portion said valve member further including an upstanding annular resilient part extending across and blocking the inner end of said air passage and which is displaceable to open and close the inner end of the air passage into said air chamber.

6. A piercing cannula of infusion and transfusion instruments, according to claim 5, including a tubular member defining the air passage between the opening in one side of said resilient valve portion, said valve portion being spaced slightly from the end of said tubular member.

7. A piercing cannula of infusion and transfusion instruments, according to claim 6, wherein the end of said aeration channel is disposed below the lower end of said tubular member defining the air passage.

8. A piercing cannula of infusion and transfusion instruments, according to claim 5, including a fluid opening defined in said closure in addition to the air opening being closed on its inside by a portion of said valve member, said valve member being of a material which can be pierced by entrance of a piercing point through the fluid opening.

9. A piercing cannula of infusion and transfusion instruments, according to claim 5, including a fluid opening defined in said closure in addition to the air opening being closed on its inside by a portion of said valve member, said valve member being of a material which can be pierced by entrance of a piercing point through the fluid opening.

10. A piercing cannula, comprising a cannula body including a first tubular member having a liquid passage therethrough and having a lower end adapted to be connected to a liquid chamber and an opposite opened piercing end terminating in a point, a second tubular member alongside said first tubular member having an air passage therethrough and having an inner end adapted to be connected to an air supply and an outer end extending outwardly from said body, said lower end of said first tubular member providing an annular wall portion, said body having a skirt portion spaced from and completely surrounding the wall portion of the lower end of said first tubular member up to a location spaced axially upwardly from the lower end thereof surrounding said second tubular member and extending below said second tubular member, said skirt portion enclosing an air chamber communicating with the lower end of said second tubular member, means defining an air passage extending through said skirt into said air chamber, and a cylindrical valve member engaged over said first tubular member and sealed therewith and having a base engaging and closing the bottom of said skirt, said valve further including a wedge-shaped side resilient portion disposed between the air passage opening of said skirt and the inner end of said second tubular member, said resilent portion being biased against the air passage opening and regulating the flow therethrough.

11. A piercing cannula, according to claim 10, wherein said cylindrical valve member includes an annular peripheral surface for the recessed area located in spaced relationship to the wall bounding the opening through said skirt portion.

* * * * *